(12) United States Patent
Marchand et al.

(10) Patent No.: US 8,003,682 B2
(45) Date of Patent: Aug. 23, 2011

(54) INDOLE COMPOUNDS, A PROCESS FOR THEIR PREPARATION AND PHARMACEUTICAL COMPOSITIONS CONTAINING THEM

(75) Inventors: Pascal Marchand, Nantes (FR); Vincent Babonneau, Thorigne-Fouillard (FR); Sylvie Piessard, Nantes (FR); Muriel Duflos, Vue (FR); Jean Albert Boutin, Suresnes (FR); Valérie Audinot, Poissy (FR); Philippe Delagrange, Issy les Moulineaux (FR); Daniel-Henri Caignard, Boisemont (FR)

(73) Assignee: Les Laboratories Servier, Suresnes Cedex (FR)

(*) Notice: Subject to any disclaimer, the term of this patent is extended or adjusted under 35 U.S.C. 154(b) by 0 days.

(21) Appl. No.: 12/311,787

(22) PCT Filed: Oct. 17, 2007

(86) PCT No.: PCT/FR2007/001707
§ 371 (c)(1),
(2), (4) Date: Nov. 9, 2009

(87) PCT Pub. No.: WO2008/049996
PCT Pub. Date: May 2, 2008

(65) Prior Publication Data
US 2010/0063128 A1    Mar. 11, 2010

(30) Foreign Application Priority Data
Oct. 18, 2006 (FR) ...................................... 06 09114

(51) Int. Cl.
*A61K 31/4045* (2006.01)
*C07D 209/12* (2006.01)
(52) U.S. Cl. ........................................ 514/419; 548/492
(58) Field of Classification Search ................. 548/492
See application file for complete search history.

(56) References Cited

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
G. Tarzia, et al., "1-(2-alkanamidoethyl)-6-methoxyindole derivatives: A new class of totent indole melatonin analogues" Journal of Medicinal Chemistry, 1997 vol. 40, No. 13, p. 2003-2010.
M. Mor, et al., "Synthesis, pharmacological characterization and QSAR studies on 2-substituted indole melatonin receptor ligands" Bioorganic and Medicinal Chemistry, 2001, vol. 9 No. 4, p. 1045-1057.
International Search Report for PCT/FR2007/001707 of Apr. 1, 2008.
Li, et al., *Drugs of the Future*, 2000, 25, 945-957.
Krause, et al., *Society for Neuroscience*, 1996, 22, No. 651.19, p. 1400.
Vacas, et al., *J. Pineal Research*, 1992, 13, 60-65.
Cagnacci, et al., *J. Pineal Research*, 1997, 22, 16-19.
Lagneux, et al., *Life Sciences*, 2000, 66, 503-509.
Brydon, et al., *Endocrinology*, 2001, 142, 4264-4271.
Bylesjö, et al., *International Journal of Eating Disorders*, 1996, 20, 443-446.
Ferrari, et al., *Biol. Psychiatry*, 1990, 27, 1007-1020.
Mazzucchelli, et al., *Molecular Brain Research*, 1996, 39, 117-126.
Brown, *CNS Drugs*, 1996, 3, 209-226.
Waldhauser, et al., *Psychopharmacology*, 1990, 100, 222-226.
Skene, et al., *Brain Research*, 1990, 528, 170-174.
Monteleone, et al., *Schizophrenia Research*, 1992, 7, 77-84.
Mc Intyre, et al., *Journal of Affective Disorders*, 1987, 12, 203-206.
Erlich, et al., *J. Neurosurg.*, 1985, 63, 321-341.
Maurizi, *Medical Hypotheses*, 1988, 27, 271-276.
Kopp, et al., *Behavioural Pharmacology*, 1999, 10, 73-83.
Kopp, et al., *Neuorpharmacology*, 2000, 39, 1865-1871.
Fanteck, et al., *Exp. Brain Res.*, 1995, 107, 321-325.
Rasmussen, et al., *Endocrinology*, 1999, 140, 1009-1012.
Armstrong, et al., *Medical Hypotheses*, 1991, 34, 300-309.
O'Brien, et al., *Clinical Endocrinology*, 1986, 24, 359-364.
Motilva, et al., *Current Pharmaceutical Design*, 2001, 7, 909-931.
Tamarkin, et al., *Science*, 1985, 227, 714-720.
Chemineau, et al., *Rec. Med. Vet.*, 1991, 167, 227-239.
Xu, et al., *Drug Development Research*, 1996, 39, 167-173.
Regrigny, et al., *Am. J. Physiol.*, 1998, 275, 139-144.
Stankov, et al., *Neuroscience*, 1993, 52, 459-468.
Leone, et al., *Cephalalgia*, 1996, 16, 494-496.
Brun, et al., *Cephalalgia*, 1995, 15, 136-139.
Ying, et al., *Eur. J. of Pharmacology*, 1993, 246, 89-96.
Laudon, et al., *Journal of Clinical Endocrinology and Metabolism*, 1996, 81, 1336-1342.
Lissoni, et al., *British Journal of Cancer*, 1996, 74, 1466-1468.

* cited by examiner

*Primary Examiner* — Shawquia Young
(74) *Attorney, Agent, or Firm* — Hueschen and Sage

(57) ABSTRACT

Compounds of formula (I):

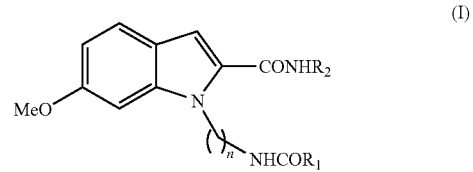

wherein:
$R_1$ represents an alkyl, cycloalkyl or cycloalkylalkyl group,
$R_2$ represents a linear or branched ($C_1$-$C_6$)alkyl group,
and n represents from 1 to 6.
Medicaments.

9 Claims, No Drawings

INDOLE COMPOUNDS, A PROCESS FOR THEIR PREPARATION AND PHARMACEUTICAL COMPOSITIONS CONTAINING THEM

The present invention relates to new indole compounds, to a process for their preparation and to pharmaceutical compositions containing them The compounds of the present invention are new and have pharmacological properties that are of great interest in relation to melatoninergic receptors.

In the last ten years, numerous studies have demonstrated the major role played by melatonin (N-acetyl-5-methoxytryptamine) in a large number of physiopathological phenomena and in the control of circadian rhythms, but melatonin has a rather short half-life owing to the fact that it is rapidly metabolised. Great interest therefore lies in the possibility of making available to the clinician melatonin analogues that are metabolically more stable and have an agonist or antagonist character and of which the therapeutic effect may be expected to be superior to that of the hormone itself.

In addition to their beneficial action in respect of circadian rhythm disorders (J. Neurosurg. 1985, 63, pp. 321-341) and sleep disorders (Psychopharmacology, 1990, 100, pp. 222-226), ligands of the melatoninergic system have valuable pharmacological properties in respect of the central nervous system, especially anxiolytic and antipsychotic properties (Neuropharmacology of Pineal Secretions, 1990, 8 (3-4), pp. 264-272), and analgesic properties (Pharmacopsychiat., 1987, 20, pp. 222-223), and also for the treatment of Parkinson's disease (J. Neurosurg. 1985, 63, pp. 321-341) and Alzheimer's disease (Brain Research, 1990, 528, pp. 170-174). The compounds have also demonstrated activity in relation to certain cancers (Melatonin—Clinical Perspectives, Oxford University Press, 1988, pp. 164-165), ovulation (Science 1987, 227, pp. 714-720), diabetes (Clinical Endocrinology, 1986, 24, pp. 359-364), and in the treatment of obesity (International Journal of Eating Disorders, 1996, 20 (4), pp. 443-446).

Those various effects are exerted via the intermediary of specific melatonin receptors. Molecular biology studies have demonstrated the existence of a number of receptor sub-types that are capable of binding that hormone (Trends Pharmacol. Sci., 1995, 16, p. 50; WO 97.04094). It has been possible for some of those receptors to be located and characterised for different species, including mammals. In order to be able to understand the physiological functions of those receptors better, it is of great advantage to have available selective ligands. Moreover such compounds, by interacting selectively with one or another of those receptors, may be excellent medicaments for the clinician in the treatment of pathologies associated with the melatoninergic system, some of which have been mentioned above.

In addition to being new, the compounds of the present invention exhibit a very strong affinity for melatonin receptors.

The present invention relates more especially to compounds of formula (I):

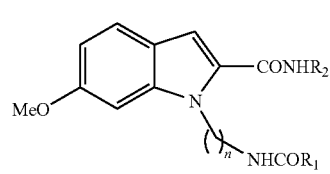

wherein:
$R_1$ represents a linear or branched $(C_1-C_6)$alkyl group, a linear or branched $(C_3-C_8)$-cycloalkyl group or a $(C_3-C_8)$cycloalkyl-$(C_1-C_6)$alkyl group in which the alkyl moiety may be linear or branched,
$R_2$ represents a linear or branched $(C_1-C_6)$alkyl group,
and n represents 1, 2, 3, 4, 5 or 6, to their enantiomers and diastereoisomers, and also to addition salts thereof with a pharmaceutically acceptable acid or base.

Among the pharmaceutically acceptable acids there may be mentioned, without implying any limitation, hydrochloric acid, hydrobromic acid, sulfuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulfonic acid, camphoric acid, oxalic acid etc.

Among the pharmaceutically acceptable bases there may be mentioned, without implying any limitation, sodium hydroxide, potassium hydroxide, triethylamine, tert-butylamine etc.

Preferred compounds according to the invention are those where n represents 2.

$R_1$ advantageously represents an alkyl group, such as, for example, a methyl or propyl group and more especially a methyl group.

Preferred $R_2$ groups are methyl, ethyl and propyl.

The invention relates even more especially to the following compounds: 1-[2-(acetylamino)ethyl]-6-methoxy-N-methyl-1H-indole-2-carboxamide, 1-[2-(acetylamino)-ethyl]-N-ethyl-6-methoxy-1H-indole-2-carboxamide and 1-[2-(acetylamino)ethyl]-6-methoxy-N-propyl-1H-indole-2-carboxamide.

The enantiomers, diastereoisomers and also addition salts with a pharmaceutically acceptable acid or base of the preferred compounds of the invention form an integral part of the invention.

The present invention relates also to a process for the preparation of compounds of formula (I), which process is characterised in that there is used as starting material the compound of formula (II):

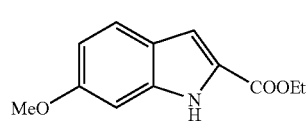

which is condensed in basic medium with chloroacetonitrile to yield the compound of formula (III):

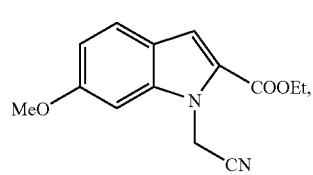

which is subjected, after reduction, to the action of an acid chloride of formula $R_1COCl$ wherein $R_1$ is as defined for formula (I) or the corresponding symmetrical anhydride to yield a compound of formula (IV):

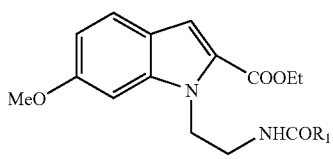

wherein $R_1$ is as defined hereinbefore,
which is hydrolysed to yield a compound of formula (V):

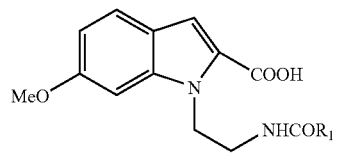

wherein $R_1$ is as defined hereinbefore,
which is condensed with a compound of formula $HNR_2R_3$ to yield a compound of formula (I),
which may be purified according to a conventional separation technique, is converted, if desired, into addition salts with a pharmaceutically acceptable base, and the enantiomers of which may be separated on a chiral column according to a conventional separation technique.

A pharmacological study of the compounds of the invention has demonstrated that they are non-toxic, have a high selective affinity for melatonin receptors and have substantial activity in respect of the central nervous system and, especially, there have been revealed therapeutic properties in respect of sleep disorders, antidepressant properties, anxiolytic properties, antipsychotic properties, analgesic properties and also properties in respect of microcirculation, enabling it to be established that the products of the invention are useful in the treatment of stress, sleep disorders, anxiety, seasonal affective disorder or major depression, cardiovascular pathologies, pathologies of the digestive system, insomnia and fatigue due to jetlag, schizophrenia, panic attacks, melancholia, appetite disorders, obesity, insomnia, psychotic disorders, epilepsy, diabetes, Parkinson's disease, senile dementia, various disorders associated with normal or pathological ageing, migraine, memory loss, Alzheimer's disease, and in cerebral circulation disorders. In another field of activity, it appears that the products of the invention can be used in the treatment of sexual dysfunction, that they have ovulation-inhibiting and immunomodulating properties and that they lend themselves to use in the treatment of cancers.

The compounds will preferably be used in the treatment of major depression, seasonal affective disorder, sleep disorders, cardiovascular pathologies, pathologies of the digestive system, insomnia and fatigue due to jetlag, appetite disorders and obesity.

For example, the compounds will be used in the treatment of major depression, seasonal affective disorder and sleep disorders.

The present invention relates also to pharmaceutical compositions comprising at least one compound of formula (I) on its own or in combination with one or more pharmaceutically acceptable excipients.

Amongst the pharmaceutical compositions according to the invention there may be mentioned more especially those which are suitable for oral, parenteral, nasal, per- or transcutaneous, rectal, perlingual, ocular or respiratory administration and especially tablets or dragées, sublingual tablets, sachets, paquets, capsules, glossettes, lozenges, suppositories, creams, ointments, dermal gels and drinkable or injectable ampoules.

The dosage varies according to the sex, age and weight of the patient, the administration route, the nature of the therapeutic indication or any associated treatments, and ranges from 0.01 mg to 1 g per 24 hours in one or more administrations.

The following Examples illustrate the invention and do not limit it in any way.

EXAMPLE 1

1-[2-(Acetylamino)ethyl]-6-methoxy-N-methyl-1H-indole-2-carboxamide

Step A: Ethyl 1-(cyanomethyl)-6-methoxy-1H-indole-2-carboxylate

Under nitrogen, dissolve 2.15 g of ethyl 6-methoxy-1H-indole-2-carboxylate in 10 ml of dimethylformamide. Add 0.59 g of sodium hydride in small portions at 0° C. and stir the reaction at 0° C. for 30 minutes. Add 0.93 ml of acetonitrile chloride at 0° C. and stir the reaction at ambient temperature for 24 hours. Add water and extract with ethyl acetate. Wash the organic phase with saturated aqueous sodium hydrogen carbonate solution and with saturated aqueous sodium chloride solution. Dry the organic phase over sodium sulfate, filter and evaporate. Purify the compound by column chromatography on silica gel using dichloromethane as eluant. The title compound is obtained in the form of a white powder.
Melting point: 145-146° C.

Step B: Ethyl 1-[2-(acetylamino)ethyl]-6-methoxy-1H-indole-2-carboxylate

Dissolve 0.34 g of the compound obtained in Step A in 10 ml of tetrahydrofuran and add a catalytic amount of Raney nickel and hydrogenate the reaction (10 bars) at ambient temperature for 24 hours. Filter over Celite and then evaporate. Take up the residue in 10 ml of tetrahydrofuran in the presence of 0.16 ml of triethylamine and, at 0° C. under argon, add dropwise 0.15 ml of acetic anhydride. Stir the reaction at ambient temperature for 22 hours. Evaporate, and take up the residue in ethyl acetate. Wash the organic phase with saturated aqueous sodium hydrogen carbonate solution and then with saturated aqueous sodium chloride solution and subsequently dry over sodium sulfate. Filter and evaporate in vacuo, and then purify the compound by column chromatography on silica gel using ethyl acetate as eluant. The title compound is isolated in the form of a white solid.
Melting point: 159-160° C.

Step C: 1-[2-(Acetylamino)ethyl]-6-methoxy-1H-indole-2-carboxylic acid

Dissolve 0.69 g of the compound obtained in Step B in 10 ml of absolute ethanol and add 2.5 ml of sodium hydroxide solution (1M) and reflux for 16 hours. Cool and add 20 ml of water and acidify the reaction mixture with hydrochloric acid (5M). Filter off the precipitate and wash it with water. The title product is obtained in the form of a white solid.
Melting point: 210-211° C.

Step D: 1-[2-(Acetylamino)ethyl]-6-methoxy-N-methyl-1H-indole-2-carboxamide

Under nitrogen, add 0.12 g of 2-chloro-1-methylpyridinium iodide, 0.32 ml of triethylamine and 0.04 ml of methylamine hydrochloride in dichloromethane to a solution of 0.13 g of the compound obtained in Step C in 20 ml of dichloromethane and then heat at reflux for 14 hours. Dilute the reaction mixture with dichloromethane and wash with saturated aqueous sodium chloride solution. Extract and dry the organic phase over sodium sulfate and then filter and evaporate. Purify the compound by column chromatography on silica gel using as eluant a 19/1 dichloromethane/ethanol mixture. After triturating in diisopropyl ether, the title compound is obtained in the form of a white solid.

Melting point: 177-178° C.

EXAMPLE 2

1-[2-(Acetylamino)ethyl]-N-ethyl-6-methoxy-1H-indole-2-carboxamide

Under nitrogen, add 0.18 g of 2-chloro-1-methylpyridinium iodide, 0.25 ml of triethylamine and 0.04 ml of ethylamine in dichloromethane to a solution of 0.20 g of the compound obtained in Step C of Example 1 in 20 ml of dichloromethane and then heat at reflux for 14 hours. Dilute the reaction mixture with dichloromethane and wash with saturated aqueous sodium chloride solution. Extract and dry the organic phase over sodium sulfate and then filter and evaporate. Purify the compound by column chromatography on silica gel using as eluant a 19/1 dichloromethane/ethanol mixture. After triturating in diisopropyl ether, the title compound is obtained in the form of a white solid.

Melting point: 135-136° C.

EXAMPLE 3

1-[2-(Acetylamino)ethyl]-6-methoxy-N-propyl-1H-indole-2-carboxamide

Under nitrogen, add 0.18 g of 2-chloro-1-methylpyridinium iodide, 0.25 ml of triethylamine and 0.06 ml of propylamine in dichloromethane to a solution of 0.20 g of the compound obtained in Step C of Example 1 in 20 ml of dichloromethane and then heat at reflux for 14 hours. Dilute the reaction mixture with dichloromethane and wash with saturated aqueous sodium chloride solution. Extract and dry the organic phase over sodium sulfate and then filter and evaporate. Purify the compound by column chromatography on silica gel using as eluant a 19/1 dichloromethane/ethanol mixture. After triturating in diisopropyl ether, the title compound is obtained in the form of a white solid.

Melting point: 127-128° C.

Pharmacological Study

EXAMPLE A

Acute Toxicity Study

The acute toxicity was evaluated after oral administration to groups each comprising 8 mice (26±2 grams). The animals were observed at regular intervals during the course of the first day, and daily for the two weeks following treatment. The $LD_{50}$ (dose that causes the death of 50% of the animals) was evaluated and demonstrated the low toxicity of the compounds of the invention.

EXAMPLE B

Forced Swimming Test

The compounds of the invention are tested in a behavioural model, the forced swimming test.

The apparatus is composed of a Plexiglas cylinder filled with water. The animals are tested individually for a session of 6 minutes. At the start of each test, the animal is placed in the centre of the cylinder. The time spent immobile is recorded. Each animal is judged to be immobile when it ceases to struggle and remains immobile at the surface of the water, making only those movements which allow it to keep its head above water.

Following administration 40 minutes before the start of the test, the compounds of the invention significantly reduce the time spent immobile, which indicates their anti-depressant activity.

EXAMPLE C

Melatonin $MT_1$ and $MT_2$ Receptor for Binding Study

The $MT_1$ or $MT_2$ receptor binding experiments are carried out using 2-[$^{125}$I]-iodomelatonin as reference radioligand. The radioactivity retained is determined using a liquid scintillation counter.

Competitive binding experiments are then carried out in triplicate using the various test compounds. A range of different concentrations is tested for each compound. The results enable the binding affinities ($K_i$) of the compounds tested to be determined.

The compounds of the invention have $K_i$ values of less than 1 μM. By way of example, the compound of Example 1 has a $K_i$ ($MT_1$) of 18 nM and a $K_i$($MT_2$) of 1 nM.

EXAMPLE D

Action of the Compounds of the Invention on the Circadian Rhythms of Locomotor Activity of the Rat The involvement of melatonin in the entrainment, by day/night alternation, of the majority of physiological, biochemical and behavioural circadian rhythms has made it possible to establish a pharmacological model for use in the search for melatoninergic ligands.

The effects of the compounds are tested on numerous parameters and, in particular, on the circadian rhythms of locomotor activity, which are a reliable indicator of the activity of the endogenous circadian clock.

In this study, the effects of such compounds on a particular experimental model, namely the rat placed in temporal isolation (permanent darkness), are evaluated.

Experimental Protocol

One-month-old male rats are subjected, as soon as they arrive at the laboratory, to a light cycle of 12 hours of light per 24 hours (LD 12:12).

After 2 to 3 weeks' adaptation, they are placed in cages fitted with a wheel connected to a recording system in order to detect the phases of locomotor activity and thus monitor the nychthemeral (LD) or circadian (DD) rhythms.

As soon as the rhythms recorded show a stable entrainment by the light cycle LD 12:12, the rats are placed in permanent darkness (DD).

Two to three weeks later, when the free-running rhythm (rhythm reflecting that of the endogenous clock) is clearly established, the rats are given a daily administration of the compound to be tested.

The observations are made by means of visualisation of the activity rhythms:
  entrainment of the activity rhythms by the light rhythm,
  disappearance of the entrainment of the rhythms in permanent darkness, entrainment by the daily administration of the compound; transitory or durable effect.

A software package makes it possible:
to measure the duration and intensity of the activity, the period of the rhythm of the animals in the free-running state and during treatment,
to demonstrate by spectral analysis the existence of circadian and non-circadian (for example ultradian) components, where present.

Results

It clearly appears that the compounds of the invention have a powerful action on the circadian rhythm via the melatoninergic system.

EXAMPLE E

Light/Dark Cages Test

The compounds of the invention are tested in a behavioural model, the light/dark cages test, which enables the anxiolytic activity of the compounds to be demonstrated.

The apparatus consists of two polyvinyl boxes covered with Plexiglas. One of the boxes is in darkness. A lamp is placed above the other box, yielding a light intensity of approximately 4000 lux at the centre of the box. An opaque plastics tunnel separates the light box from the dark box. The animals are tested individually for a session of 5 minutes. The floor of each box is cleaned between each session. At the start of each test, the mouse is placed in the tunnel, facing the dark box. The time spent by the mouse in the illuminated box and the number of passages through the tunnel are recorded after the first entry into the dark box.

Following administration of the compounds 30 minutes before the start of the test, the compounds of the invention significantly increase the time spent in the illuminated cage and the number of passages through the tunnel, which demonstrates the anxiolytic activity of the compounds of the invention.

EXAMPLE F

Pharmaceutical Composition: Tablets

| | |
|---|---|
| 1000 tablets each containing a dose of 5 mg of 1-[2-(acetylamino)ethyl]-6-methoxy-N-methyl-1H-indole-2-carboxamide (Example 1) | 5 g |
| wheat starch | 20 g |
| maize starch | 20 g |
| lactose | 30 g |
| magnesium stearate | 2 g |
| silica | 1 g |
| hydroxypropyl cellulose | 2 g |

The invention claimed is:

1. A compound selected from those of formula (I):

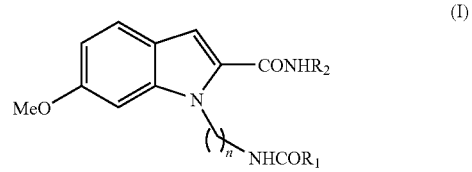

(I)

wherein:
R$_1$ represents a linear or branched (C$_1$-C$_6$)alkyl group, a linear or branched (C$_3$-C$_8$)-cycloalkyl group or a (C$_3$-C$_8$)cycloalkyl-(C$_1$-C$_6$)alkyl group in which the alkyl moiety may be linear or branched,
R$_2$ represents a linear or branched (C$_1$-C$_6$)alkyl group,
and n represents 1, 2, 3, 4, 5 or 6,
its enantiomers and diastereoisomers, and addition salts thereof with a pharmaceutically acceptable acid or base.

2. The compound of claim 1, wherein n represents 2.

3. The compound of claim 1, wherein R$_1$ represents a methyl group.

4. The compound of claim 1, wherein R$_2$ represents a methyl, ethyl or propyl group.

5. The compound of claim 1 which is 1-[2-(acetylamino)ethyl]-6-methoxy-N-methyl-1H-indole-2-carboxamide, or an addition salt thereof with a pharmaceutically acceptable acid or base.

6. The compound of claim 1 which is 1-[2-(acetylamino)ethyl]-N-ethyl-6-methoxy-1H-indole-2-carboxamide, or an addition salt thereof with a pharmaceutically acceptable acid or base.

7. The compound of claim 1 which is 1-[2-(acetylamino)ethyl]-6-methoxy-N-propyl-1H-indole-2-carboxamide, or an addition salt thereof with a pharmaceutically acceptable acid or base.

8. A pharmaceutical composition comprising at least one compound of claim 1, or an addition salt thereof with a pharmaceutically acceptable acid or base, in combination with one or more pharmaceutically acceptable excipients.

9. A method for treating a living animal body, including a human, afflicted with a condition selected from stress, anxiety, major depression or seasonal affective disorder, insomnia and fatigue due to jetlag, panic attacks, and insomnia, comprising the step of administering to the living animal body, including a human, a therapeutically effective amount of the compound of claim 1.

* * * * *